United States Patent
Ward (10) Patent No.: US 12,357,818 B2
(45) Date of Patent: Jul. 15, 2025

(54) METHOD OF PERCUTANEOUSLY IMPLANTING A MEDICAL IMPLANT AND A DELIVERY DEVICE FOR PERCUTANEOUS DELIVERY OF A MEDICAL IMPLANT

(71) Applicant: Capri Medical Limited, Dublin (IE)

(72) Inventor: Fergal Ward, Dublin (IE)

(73) Assignee: Capri Medical Limited, Ballsbridge (IE)

( * ) Notice: Subject to any disclaimer, the term of this patent is extended or adjusted under 35 U.S.C. 154(b) by 328 days.

(21) Appl. No.: 17/840,994

(22) Filed: Jun. 15, 2022

(65) Prior Publication Data

US 2023/0405309 A1 Dec. 21, 2023

(51) Int. Cl.
*A61N 1/05* (2006.01)
*A61B 17/34* (2006.01)
*A61N 1/372* (2006.01)

(52) U.S. Cl.
CPC ....... *A61N 1/0551* (2013.01); *A61N 1/37205* (2013.01); *A61B 17/3468* (2013.01)

(58) Field of Classification Search
CPC ............. A61N 1/0551; A61N 1/37205; A61N 1/3787; A61B 17/3468
See application file for complete search history.

(56) References Cited

U.S. PATENT DOCUMENTS

| | | | |
|---|---|---|---|
| 6,269,270 B1* | 7/2001 | Boveja | A61N 1/0551 607/45 |
| 2002/0055761 A1* | 5/2002 | Mann | A61N 1/36071 607/41 |
| 2019/0290908 A1* | 9/2019 | Hsu | A61N 1/37217 |
| 2021/0282888 A1* | 9/2021 | Rebellino | A61M 37/0069 |
| 2022/0226018 A1* | 7/2022 | Virden | A61M 37/0069 |

* cited by examiner

*Primary Examiner* — Mark W. Bockelman
(74) *Attorney, Agent, or Firm* — ArentFox Schiff LLP; Bruce D. Jobse (57) ABSTRACT

A method of percutaneously implanting a neurostimulator implant in tissue of a patient, the neurostimulator implant having a wireless power receiver and an elongate electrode lead, includes percutaneously implanting the neurostimulator implant such that the wireless power receiver is oriented towards the skin surface of the patient at the implantation site.

23 Claims, 10 Drawing Sheets

METHOD OF PERCUTANEOUSLY IMPLANTING A MEDICAL IMPLANT AND A DELIVERY DEVICE FOR PERCUTANEOUS DELIVERY OF A MEDICAL IMPLANT

FIELD OF THE INVENTION

This invention relates to a method of percutaneously implanting a medical implant, and a delivery system for percutaneous delivery of a medical implant, such as a neuromodulation implant, into a patient's tissue.

BACKGROUND

It is known to provide an implantable neurostimulator comprising a housing and an electrode. A power antenna, microcontroller, and communication antenna are disposed in the housing for receiving power from an external source and receiving/transmitting sensor information relating to the electrode. A delivery system can be used to position the neurostimulator in a patient, in particular proximate to a nerve, by cutting an opening in the patient and passing the delivery system into the opening to position the implantable neurostimulator.

BRIEF SUMMARY OF THE DISCLOSURE

In accordance with a first aspect of the present disclosure there is provided a method of percutaneously implanting a medical implant in tissue of a patient, the medical implant comprising a wireless power receiver and an elongate electrode lead, wherein the method comprises percutaneously implanting the medical implant such that the wireless power receiver is oriented towards the skin surface of the patient at the implantation site.

Accordingly, wireless power transmission between the medical implant and an external wireless power transmitted can be improved.

In examples, the method may comprise percutaneously implanting the medical implant such that the wireless power receiver is oriented within about 20 degrees of a normal line from the skin surface of the patient at the implantation site, preferably within about 10 degrees of the normal line from the skin surface of the patient at the implantation site, more preferably within about 5 degrees of the normal line from the skin surface of the patient at the implantation site.

In examples, the method may comprise percutaneously implanting the medical implant such that the wireless power receiver is oriented substantially parallel to a normal line from the skin surface of the patient at the implantation site.

In examples, the wireless power receiver may comprise an antenna receiver for receiving wireless power by wireless power coupling. In such examples, the antenna receiver may have a power-receiving direction, and the medical implant may be percutaneously implanted such that the power-receiving direction of the antenna receiver is oriented towards the skin surface of the patient.

In examples, the medical implant may comprise a housing having an antenna portion configured to act as a wireless power receiver. The antenna portion may have a power-receiving direction, and the medical implant may be percutaneously implanted such that the power-receiving direction of the antenna portion of the housing is oriented towards the skin surface of the patient.

In examples, the medical implant may comprise an elongate housing portion holding the wireless power receiver. The wireless power receiver may be oriented substantially perpendicularly to the elongate housing portion. The method may comprise percutaneously implanting the medical implant such that the housing portion is substantially parallel to the skin surface of the patient at the implantation site.

In examples, the housing portion may comprise a wall having a wireless power transmission window for transmission of wireless power through the wall of the housing portion. The method may comprise percutaneously implanting the medical implant such that the wireless power transmission window is directed towards the skin of the patient at the implantation site.

In examples, the method may comprise simultaneously percutaneously implanting the housing portion and the electrode lead of the medical implant. In examples, the method may comprise percutaneously implanting the electrode lead at a greater depth than the housing portion. In examples, the electrode lead may be implanted at an angle relative to the housing portion. In examples, the method may comprise percutaneously implanting the electrode lead proximal to a nerve of the patient, and percutaneously implanting the housing portion in subcutaneous tissue of the patient.

In examples, the medical implant may comprise an elongate housing portion holding the wireless power receiver. In such examples, the method may comprise percutaneously implanting the electrode lead at a non-parallel angle relative to the elongate housing portion. In examples, the method may comprise percutaneously implanting the elongate housing portion such that the axial direction of the electrode lead is approximately perpendicular to the elongate housing portion. That is, the electrode lead may be angled with respect to the housing portion. Accordingly, the electrode lead can be appropriately positioned in the tissue and the housing portion (and wireless power receiver) can be oriented to receive wireless power.

In examples, the method may comprise percutaneously implanting the electrode lead while the elongate housing portion is substantially parallel to the electrode lead, and, once the electrode lead is implanted, positioning the elongate housing portion such that the wireless power receiver is oriented towards the skin of the patient at the implantation site.

In examples, the method may comprise using a delivery device to percutaneously implant the medical implant. The delivery device may comprise a delivery sheath holding the medical implant, and the method may comprise percutaneously positioning the delivery sheath to percutaneously implant the medical implant.

In examples, the delivery sheath may comprise a first part for percutaneously implanting a housing portion of the medical implant holding the wireless power receiver, and a second part for percutaneously implanting the electrode lead. The second part of the delivery sheath may be parallel with and extend beyond the first part of the delivery sheath.

In examples, the second part of the delivery sheath may be retractable relative to the first part of the delivery sheath. The method may comprise percutaneously positioning the first part of the delivery sheath at a first depth, percutaneously positioning the second part of the delivery sheath at a second depth, retracting the second part of the delivery sheath to implant the electrode lead, and ejecting the housing portion from the first part of the delivery sheath.

In examples, the first part of the delivery sheath may have an axial direction, and the housing portion may be ejected from the first part of the delivery sheath in a direction non-parallel to axial direction of the first part of the delivery sheath. For example, the housing portion may be ejected from the first part of the delivery sheath through a side opening in the first part of the delivery sheath. In examples, the housing portion is rotated as it is ejected from the first part of the delivery sheath.

In examples, the delivery device may comprise a pusher operable to eject the housing portion from the first part of the delivery sheath. The method may comprise operating the pusher to eject the housing portion from the first part of the delivery sheath.

In examples, the medical implant may be a neurostimulator implant operate to stimulate a nerve of the patient. In other examples, the medical implant may be a diagnostic implant, particularly a diagnostic implant operable to detect neural signals. In other examples, the diagnostic implant may detect one or more patient vital signs, for example body temperature, heart rate, electromyography (EMG), electrocardiogram (ECG), respiration rate, blood pressure, and/or blood gas concentration (e.g., oxygen, carbon dioxide, carbon monoxide).

In examples, the medical implant may further comprise a wireless power transmitter. In examples, the medical implant may be operable as a wireless power relay for providing wireless power to a further medical implant.

In accordance with a second aspect of the present disclosure, there is also provided a delivery device for percutaneous delivery of a medical implant into a patient's tissue, the delivery device comprising:

a delivery sheath having a lumen adapted to hold the medical implant, the delivery sheath being percutaneously positionable for implanting the medical implant into the patient's tissue;

and wherein the delivery sheath comprises a side wall having a side opening through which at least a part of the medical implant is ejected during use.

Advantageously, the side opening allows at least a part of the medical implant to be ejected in a direction non-parallel to the delivery sheath, allowing a wireless power receiver of the medical implant to be directed towards the skin of the patient.

In examples, the medical implant may comprise a housing portion and an elongate electrode lead extending from the housing portion. In examples, the delivery sheath may comprise a first part adapted to hold the housing portion, and a second part adapted to carry the elongate electrode lead. The first part of the delivery sheath may comprise the side opening for ejection of the housing portion during implantation. Accordingly, the housing portion can be implanted non-parallel to the electrode lead.

In examples, the side opening may extend to a tip of the first part of the delivery sheath. In examples, the first part of the delivery sheath comprises a slot along one side, the slot comprising the side opening.

In examples, the second part of the delivery sheath may be retractable relative to the first part of the delivery sheath for implanting the elongate electrode lead. In examples, the second part of the delivery sheath may comprise a slot extending along the side of the second part of the delivery sheath.

In examples, the delivery device may further comprise a pusher operable to push the part of the medical implant through the side opening during use.

In examples, the delivery device may further comprise a guide disposed in the delivery sheath and arranged to guide the part of the medical implant that is ejected through the side opening during use. In examples, the guide is shaped to rotate the part of the medical implant as it is ejected through the side opening.

In examples, the delivery sheath may comprise a needle and/or a cannula.

According to a third aspect of the present disclosure, there is also provided a method of percutaneously implanting a medical implant into a patient's tissue, the method comprising:

providing a delivery device comprising a delivery sheath having a lumen and a side wall having a side opening,
providing a medical implant in the lumen of the delivery sheath,
percutaneously positioning the delivery sheath in the patient's tissue, and
ejecting at least a part of the medical implant through the side opening of the delivery sheath.

Advantageously, the side opening allows at least a part of the medical implant to be ejected in a direction non-parallel to the delivery sheath, allowing a wireless power receiver of the medical implant to be directed towards the skin of the patient.

In examples, the medical implant may comprise a housing portion having a wireless power receiver. The method may comprise ejecting the housing portion of the medical implant through the side opening of the delivery sheath such that the wireless power receiver is oriented towards the skin of the patient at the implantation site.

In examples, the method may comprise rotating the housing portion of the medical implant as it is ejected through the side opening in the delivery sheath. In examples, the method may comprise pushing the housing portion of the medical implant through the side opening in the delivery sheath.

In examples, the medical implant further comprises an elongate electrode lead. The method may comprise percutaneously implanting the electrode lead, and ejecting the housing portion through the side opening of the delivery sheath. Accordingly, the electrode lead and housing portion can be implanted non-parallel to each other.

In examples, the delivery sheath may comprise a first part having a lumen adapted to hold the housing portion, and a second part that extends beyond the first part of the delivery sheath and is adapted to carry the elongate electrode lead. The method may comprise retracting the second part of the delivery sheath to implant the elongate electrode lead.

In examples, the medical implant may be a neurostimulator implant operate to stimulate a nerve of the patient. In other examples, the medical implant may be a diagnostic implant, particularly a diagnostic implant operable to detect neural signals. In other examples, the diagnostic implant may detect one or more patient vital signs, for example body temperature, heart rate, electromyography (EMG), electrocardiogram (ECG), respiration rate, blood pressure, and/or blood gas concentration (e.g., oxygen, carbon dioxide, carbon monoxide).

In examples, the medical implant may comprise a wireless power receiver and a wireless power transmitter. The medical implant may be operable as a wireless power relay for providing wireless power to a further medical implant.

BRIEF DESCRIPTION OF THE DRAWINGS

Embodiments of the invention are further described hereinafter with reference to the accompanying drawings, in which.

DETAILED DESCRIPTION

Figure 1:
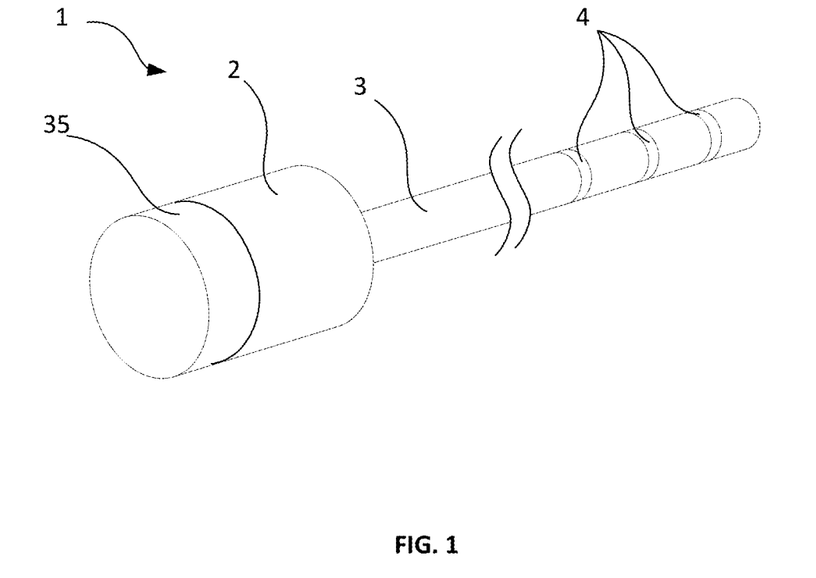
FIG. 1 shows a medical implant.

FIG. 1 schematically illustrates a medical implant 1. In examples, the medical implant 1 may be a neurostimulator implant or a diagnostic implant. The medical implant 1 comprises a housing portion 2 and an elongate electrode lead 3. The housing portion 2 may house electronics components of the medical implant 1, including for example a printed circuit board, a wireless communications receiver/transmitter, and/or sensor electronics, as described further hereinafter. In examples, the housing portion is hermetically sealed. The housing portion 2 may comprise a cylindrical casing with sealed ends, or may comprise a wrapping or other envelopment of the components within the housing portion 2.

As illustrated, the housing portion comprises a wireless power receiver 35. The wireless power receiver 35 may comprise an antenna receiver (e.g., a coil) or it may comprise a conductive portion of the housing portion 2. The wireless power receiver 35 is adapted to wireless couple with an external device to receive wireless power, as described further hereinafter.

In examples, the electrode lead 3 extends from the housing portion 2 and is flexible. The electrode lead 3 includes at least one electrode 4, in some examples multiple electrodes 4 spaced along the length of the electrode lead 3. The electrodes 4 are connected to the electronics within the housing portion 2.

In examples, the housing portion 2 may have a diameter of between about 0.5 millimetres and about 5 millimetres, for example between about 1 millimetre and about 3 millimetres. The housing portion 2 may have a length of up to about 10 millimetres, for example up to about 5 millimetres. In examples, the electrode lead 3 may have a diameter of between about 0.3 millimetres to about 1.5 millimetres, for example between about 0.5 millimetres and 1.3 millimetres. The electrode lead 3 may have a length of up to about 10 millimetres, for example up to about 50 millimetres, for example about 50 millimetres. However, it will be appreciated that the dimensions of the housing portion 2 would correspond to the size of the electronics housed within the housing portion 2, and the length of the electrode lead 3 would correspond to the anatomy surrounding the targeted nerve, so a shorter or longer electrode lead 3 may be appropriate depending on the depth of the nerve within the muscle tissue As described further hereinafter, the medical implant 1 is implantable in a patient, for example to sense and/or stimulate a nerve. In some examples, the medical implant 1 is implantable to sense and/or stimulate the greater occipital nerve, although the same or similar implant may be implantable to sense and/or stimulate other nerves, particularly other peripheral nerves of the peripheral nervous system. In examples, the medical implant 1 may be implantable to sense and/or stimulate the tibial nerve, the sacral nerve (e.g., to treat urinary incontinence) or the vagus nerve (e.g., to regulate pancreatic secretion).

Figure 2:
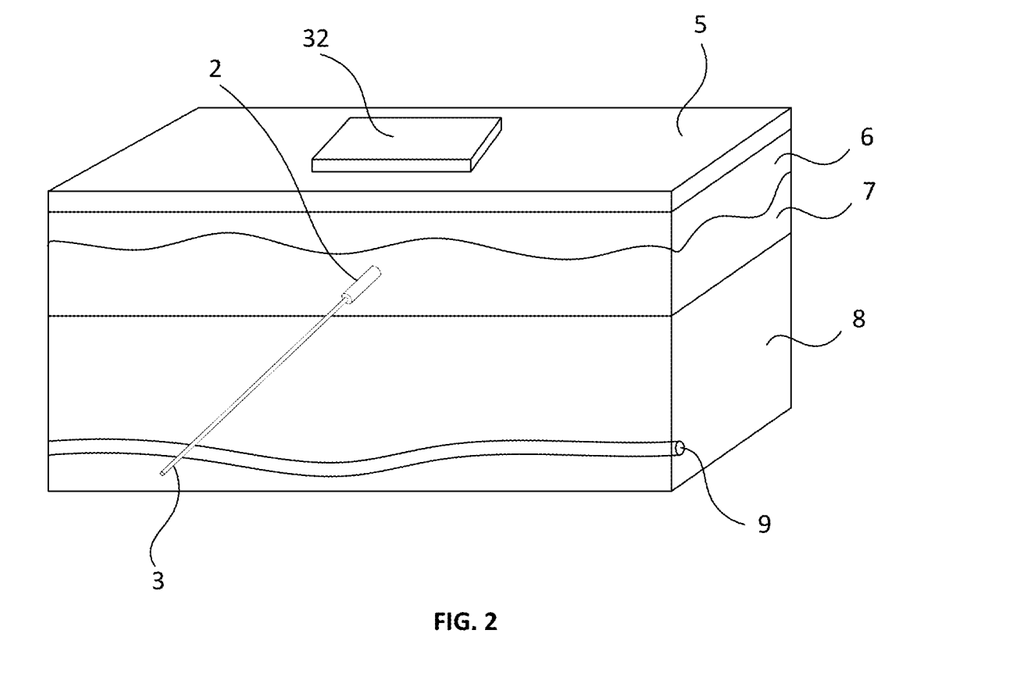
FIG. 2 show the medical implant in position in a patient, particularly in a subcutaneous position.

FIG. 2 shows the medical implant 1 once implanted in a patient. The medical implant 1 is positioned below the surface of the skin, in particular below the epidermis 5. The housing portion 2 may be positioned in the dermis 6 or in the subcutaneous tissue 7. Positioning the housing portion 2 in the subcutaneous tissue 7 may be beneficial to cause less damage and/or irritation to the patient.

As illustrated, the electrode lead 3 extends from the housing portion 2, through the underlying tissue, in particular muscle 8, to a position proximal to the target nerve 9. The electrode lead 3 is positioned such that the electrodes (4, see FIG. 1) are in contact with or proximal to the nerve 9, and so the electrodes 4 can be used to sense and/or stimulate the nerve 9.

The medical implant 1 may also include one or more anti-migration members. The anti-migration members may be provided on the housing portion 2 and/or on the electrode lead 3 and function to hold the medical implant 1 in position in the patient's tissue.

In examples, the medical implant 2 is battery-less, and does not have an integrated power source. An external device 32 can wirelessly power the medical implant 1 via the wireless power receiver 35 illustrated in FIG. 1. The external device 32 may additionally wirelessly communicate with the medical implant 1, in particular the electronics in the housing portion 2. The medical implant 1 may contain a wireless communications receiver/transmitter for communicating with the external device 32. The medical implant 1 may also have a processor or controller configured to operate the medical implant 1. The external device 32 may be positioned on the skin proximal to the medical implant 1. The external device 32 may be adhered to the skin proximal to the medical implant 1. The external device 32 may be a wearable device.

In examples, the medical implant 1 is a neurostimulator implant. The medical implant 1 may be implanted to target a particular nerve or nerve grouping, such as the greater occipital nerve.

In operation, the electrodes 4 of a neurostimulator implant are provided with an electrical signal, such as a current, to stimulate the nerve. In examples, the electrical signal may be a voltage-regulated stimulation. Such stimulation can provide relief for chronic pain, for example occipital neuralgia, intractable migraine, and/or other therapeutic benefits. In various examples the neurostimulator implant may target specific deep subcortical, cortical, spinal, cranial, and peripheral nerve structures, for treatment of pain in patients. Neurostimulation is an alternative to pain medication and nerve block injections. It is associated with fewer side effects than many medications and can reduce the potential for drug dependency.

In other examples, the medical implant 1 may be a diagnostic implant, for example a neurodiagnostic implant, operable to detect one or more neural signals in a nerve. In such examples the electrodes 4 are operable to detect neural signals. The neural signals may be analysed for the purposes of detecting, monitoring and/or diagnosing a condition. The neurodiagnostic implant 1 may target the same nerves as mentioned above for the neurostimulator implant 1.

In other examples, the diagnostic implant may additionally or alternatively detect one or more patient vital signs, for example body temperature, heart rate, electromyography (EMG), electrocardiogram (ECG), respiration rate, blood pressure, and/or blood gas concentration (e.g., oxygen, carbon dioxide, carbon monoxide).

Figure 3A:
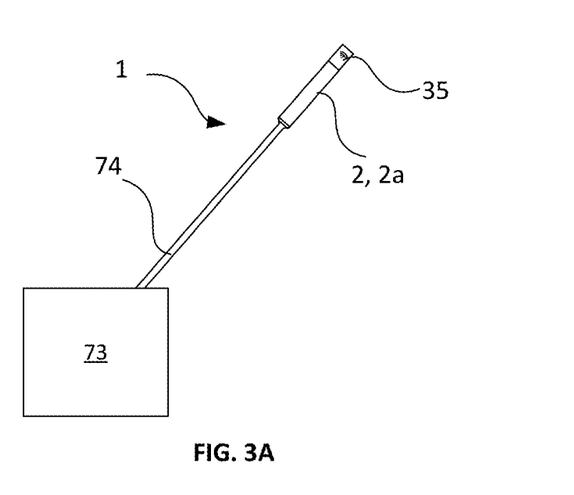
FIGS. 3A and 3B show further example medical implants acting as wireless power relays for a further medical implant.
Figure 3B:
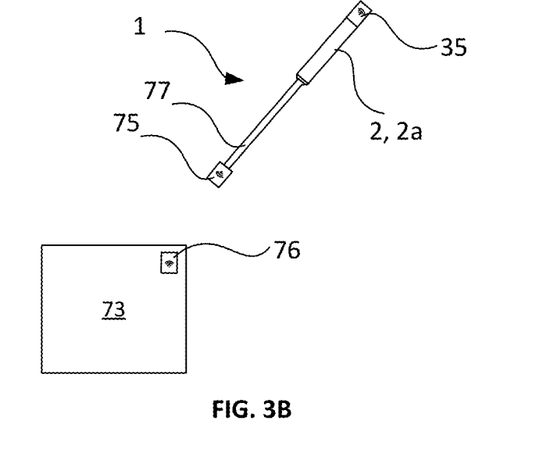

FIGS. 3A and 3B illustrate an alternative medical implant 1, for use in conjunction with a further medical implant 73. The further medical implant 73 may be a deep tissue implant, for example a pacemaker. In these examples, the medical implant 1 can act as a wireless power receiver or as a wireless power relay for the further medical implant 73. In the example of FIG. 3A the medical implant 1 may be connected to the further medical implant 73 by a wire 74. The medical implant 1 comprises a wireless power receiver 35 as described above, and transfers power to the further medical implant 73 via the wire 74. The medical implant 1 can be implanted at a lower depth in the tissue than the further medical implant 73, providing improved wireless power coupling due to the decreased distance from the external wireless power transmitter. In the example of FIG. 3B, the medical implant comprises a wireless power receiver 35 and a wireless power transmitter 75 and is arranged to relay power to a wireless power receiver 76 of the further medical implant 73. The wireless power transmitter 75 of the medical implant 1 may be connected to the housing portion 2 by a wire 77, as illustrated, or it may be within the housing portion 2 and the wire 77 may be omitted. The medical implant 1 can be implanted at a lower depth in the tissue than the further medical implant 73, providing improved wireless power coupling.

As mentioned above, the medical implant 1 is powered by wireless power transfer (WPT) from an external device 32. The efficiency of WPT is dependent on the proximity of the medical implant 1 to the wireless power transmitter in the external device 32. The efficiency of WPT is also affected by the orientation of the medical implant relative to the wireless power transmitter, and even a slight movement can cause loss of WPT, or reduction in WPT efficiency.

In some examples, the medical implant 1 may comprise an internal battery, and the battery may be recharged by wireless power transfer in the same manner as described above. In such cases, the external device 32 may be periodically used to charge the medical implant 1.

The description of the wireless power receiver 35 of the medical implant 1 relates to electrically small antennas, meaning that the antennas herein have a physical size of less than the wave length of the operating frequency. In view of this, the terms near-field, mid-field and far-field can be considered as different operating regions depending on the operating frequency and a distance between a transmitter antenna and a receiver antenna. Near-field may be considered when the distance between the transmitter antenna and the receiver antenna is less than one wave length of the operating frequency, mid-field may be considered when the distance between the transmitter antenna and the receiver antenna is close or on the boarder of one wavelength of the operating frequency, and far-field may be considered when the distance between the transmitter antenna and receiver antenna is more than one wave length of the operating frequency.

Examples disclosed herein relate to wireless power transfer systems, transmitters, receivers, transmitter antennas and receiver antennas that are configured to enable wireless power transmission with the view to power a medical implant and/or to recharge a battery forming part of a medical implant.

The medical implant comprises a wireless power receiver 35 arranged to wirelessly couple with a wireless power transmitter of an external device 32. The wireless power transmitter of the external device 32 and the wireless power receiver 35 may be configured to operate in the following frequency bands; the ultra-high frequency band (UHF), L-band, S-band, C-band and X-band. This means that the system is adaptable and can operate across 30 MHz to 12 GHz such that the wireless power transfer is flexible with regards to the distance between the receiver and the transmitter.

In one example, the wireless power receiver 35 is configured to receive transmitted wireless power transmission from the wireless power transmitter over a distance from 1 cm to 10 cm. The system enables the wireless power transfer to be performed across this distance and as such the system can operate in near-field, mid-field and far-field.

Figure 4:
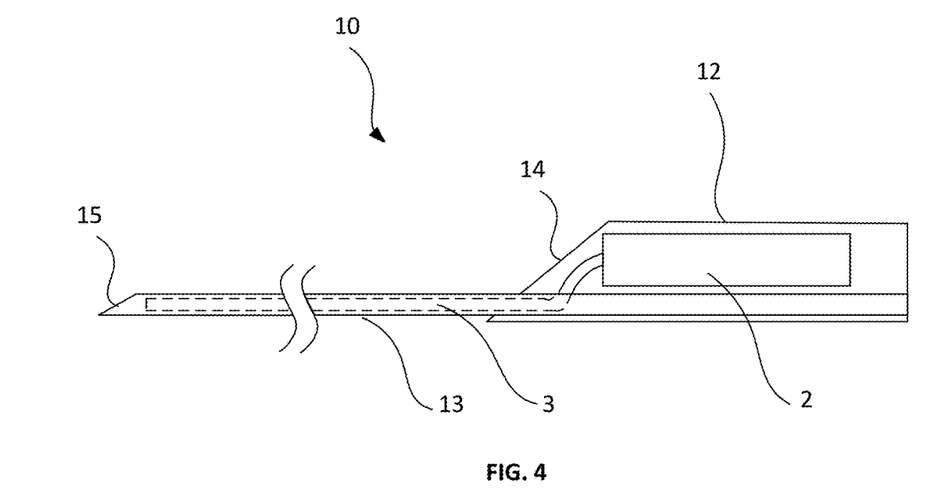
FIG. 4 shows a schematic cross-section of a delivery sheath of a delivery device for implanting the medical implant into the patient, particularly a first needle and a second needle of the delivery device.

FIGS. 4 to 7B illustrate a first example implant delivery device 10. As shown in FIG. 4, the implant delivery device 10 includes a delivery sheath. In this example the delivery sheath comprises a first needle 12 and a second needle 13. The first and second needles 12, 13 are parallel and both extend in a longitudinal direction. The second needle 13 extends further than the first needle 12. In particular, the first needle 12 has a tip 14, such as a bevel tip, and the second needle 13 extends past the tip 14 of the second needle. The second needle 13 also has a tip 15, in particular a bevel tip. The second needle 13 has a higher gauge than the first needle 12, and in particular the second needle 13 has a smaller diameter than the first needle 12.

During use, the implant housing 2 is received in the first needle 12, in particular in a lumen of the first needle 12. During use, the electrode lead 3 is received in the second needle 13, in particular in a lumen of the second needle 13. The electrode lead 3 extends along a substantial part of the second needle 13 towards the tip 15, as illustrated. A part of the electrode lead 3 adjacent to the implant housing 2 extends through an opening in the second needle 13, as described further with reference to FIG. 6. Accordingly, during use the medical implant 1 is housed within the first and second needles 12, 13 of the delivery device 10.

As shown in FIG. 4, the first needle 12 and the second needle 13 are axially offset. In particular, a central axis of the first needle 12 is offset from a central axis of the second needle 13. In the illustrated example the second needle 13 extends into the first needle 12 (in particular into the lumen of the first needle), such that the second needle 13 is partly accommodated within the first needle 12 alongside the implant housing 2.

Figure 6:
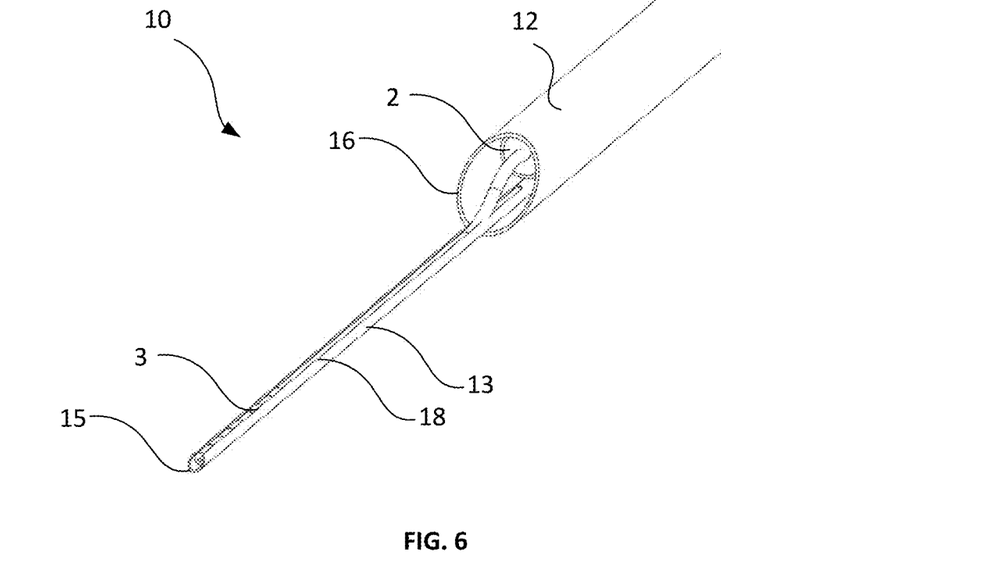
FIG. 6 shows a perspective view of an end of the first needle and the second needle, and a medical implant retained by the first and second needles.

Referring to FIG. 6, the second needle 13 includes a slot 18 to permit a part of the electrode lead 3 to extend out of the second needle 13 and connect to the implant housing 2, as shown in FIG. 4. The slot 18 may extend to the tip 15 of the second needle 13, as described further hereinafter.

In some examples the second needle 13 may comprise a sheath, having an opening extending entirely or substantially along one side.

As described in further detail hereinafter, during use the first needle 12 and the second needle 13 both penetrate the patient's skin to simultaneously position the implant housing 2 at a first depth and the electrode lead 3 at a second depth within the patient. The implant delivery device 10 then releases and deploys the medical implant 1 to leave the medical implant 1 in the position illustrated in FIG. 2. The tips 14, 15 of the first and second needles 12, 13, respectively, are sharp tips adapted to pierce the patient's skin and penetrate the tissue to position the first and second needles 12, 13 at the appropriate depth. The tips 14, 15 may be bevel tips, as would be known to the skilled person.

In examples, the first needle 12 may have a gauge of between 6 gauge and 15 gauge, for example 10 gauge. In examples, the second needle 13 may have gauge of between 15 gauge and 25 gauge, for example 20 gauge.

In various examples described hereinafter, the second needle 13 is retractable relative to the first needle 12, to deploy the electrode lead 3. The slot 18 (see FIG. 6) along the second needle 13 permits deployment of the electrode lead 3.

In examples, the implant housing 2 is releasably attached to the first needle 12 (or another part of the implant delivery device 10) and is released prior to deployment.

In examples, the implant housing 2 may be deployed from the first needle 12 simply by pulling the implant delivery device away from the patient and relying on friction between the electrode lead 3 and the patient's tissue to hold the medical implant in place and pull the implant housing 2 from the first needle 12. In other examples, the implant delivery device 10 may include a deployment member adapted to push the implant housing 2 out of the first needle 12 to deploy the implant housing 2 at the appropriate anatomical site.

Figure 5A:
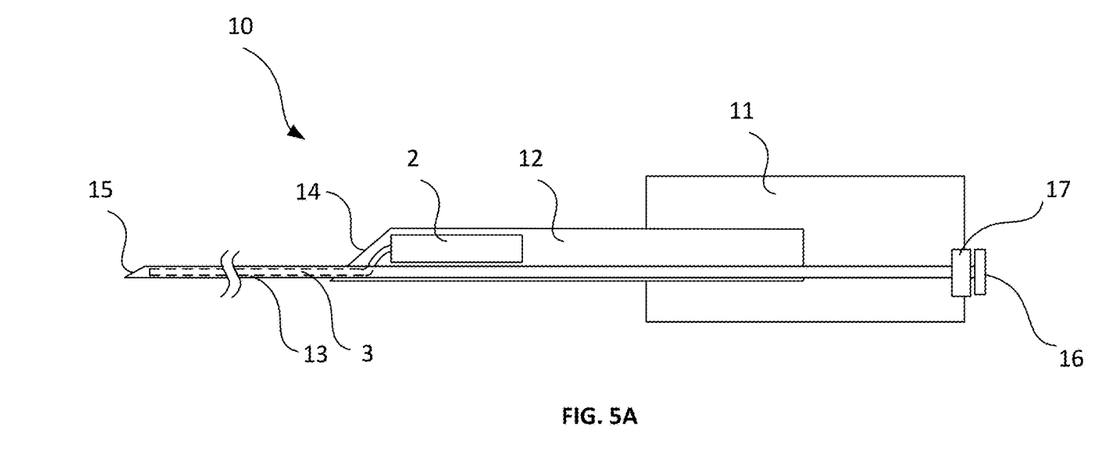
FIGS. 5A to 5C show schematic cross-sections of the delivery device, including a handle, during implantation of the medical implant.
Figure 5B:
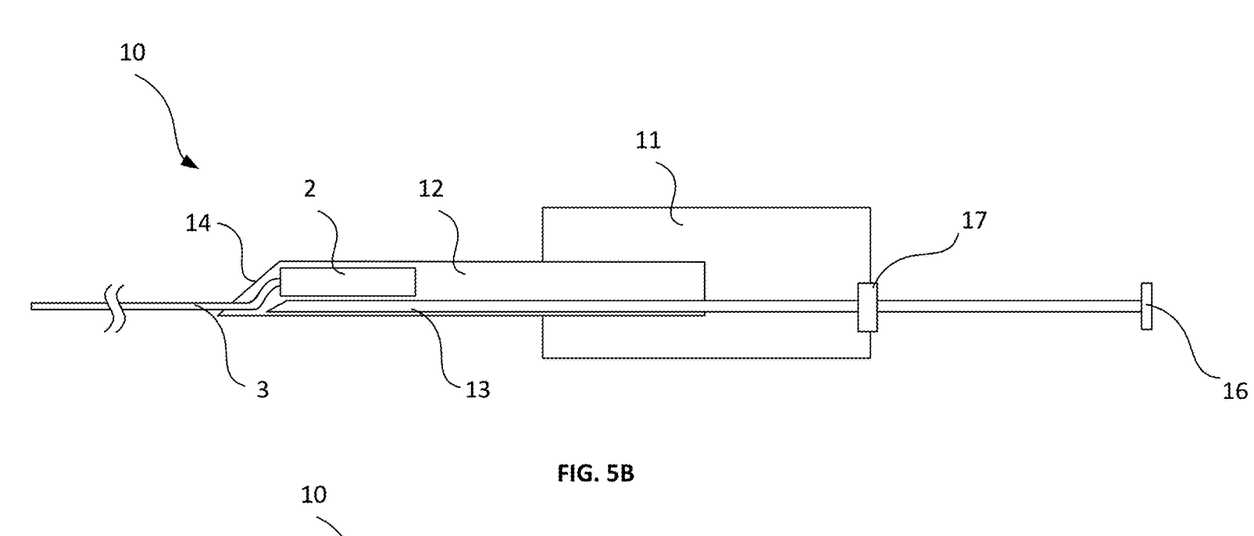
Figure 5C:
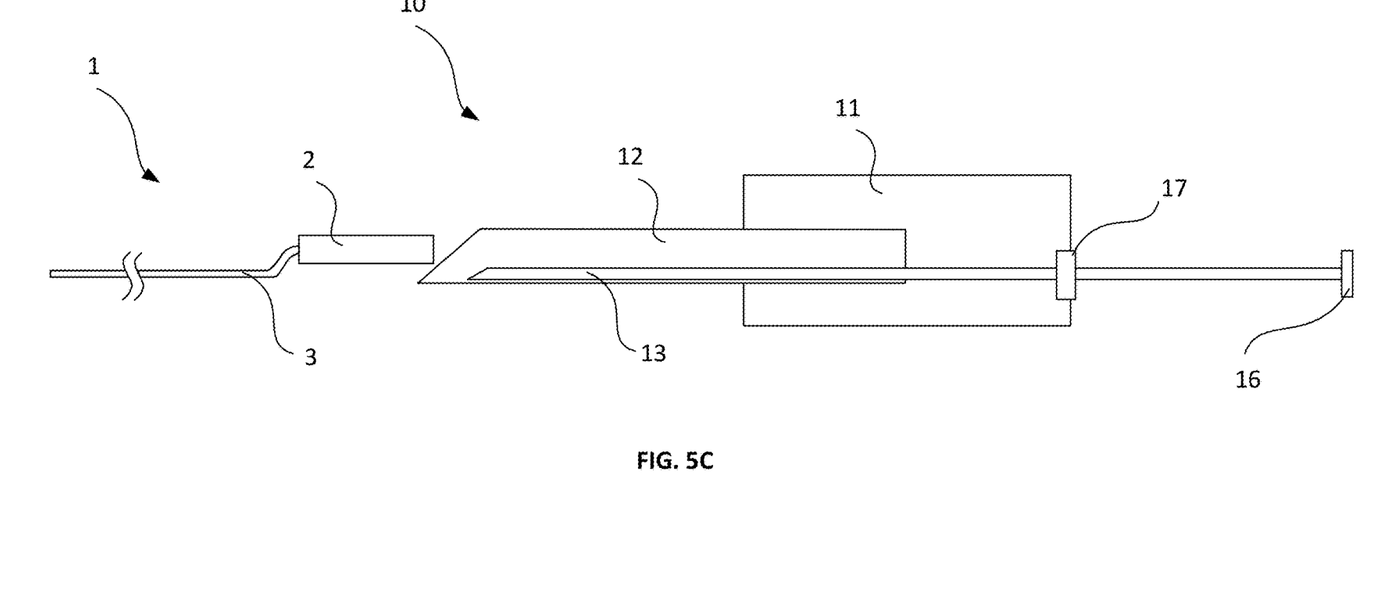

FIGS. 5A to 5C illustrate operation of the delivery device 10.

As illustrated, the example implant delivery device 10 further includes a handle 11. The handle 11 is adapted to be held by an operator. The first needle 12 is fixed to the handle 11.

The second needle 13 extends through the first needle 12 and through the handle 11. An actuation tab 16 is provided on an end of the second needle 13 opposite to the tip 15. In particular, the actuation tab 16 may be a gripping handle or similar for the operator to grip.

The second needle 13 is retractable relative to the first needle 12. In particular, the second needle 13 can slide through the first needle 12 and handle 11, from the position shown in FIG. 5A to the position shown in FIG. 5B. In this example, the second needle 13 is retractable by pulling the actuation tab 16 in a direction away from the patient. Retracting the second needle 13 in this way deploys the electrode lead 3. The opening 18 (see FIG. 6) along the second needle 13 provides for the part of the electrode lead 3 that connects to the housing portion 2. The opening 18 extends to the tip 15 of the second needle 13.

A locking device 17 is provided to lock the second needle 13 to the handle 11 and/or first needle 12. As shown, the locking device 17 may be provided at or near the actuation tab 16, and in examples locks the actuation tab 16 and/or the second needle 13 to the handle 11. The locking device 17 locks the second needle 13 in the extended position shown in FIG. 5B.

In the position shown in FIG. 5A the operator can percutaneously position the implant delivery device 10 in the patient's tissue. The position of the second needle 13 is locked relative to the handle 11, so the operator can push the implant delivery device 10 into the patient by the handle 11.

Referring to FIGS. 5A and 2, as the implant delivery device 10 is pushed into the patient the second needle 13 first penetrates the skin 5, and as the implant delivery device is pushed further the first needle 12 then penetrates the skin 5. The first and second needles 12, 13 are thereby positioned at the appropriate depths in the patient, and the housing portion 2 and electrode lead 3 are also simultaneously positioned at the appropriate depths. Therefore, the implant delivery device 10 provides percutaneous delivery of the medical implant 1 into the patient's tissue.

In examples, the operator may use an ultrasound imaging device to monitor the positions of the second needle 13 (and the first needle 12) to guide the second needle 13 towards the target nerve 9.

Once the implant delivery device 10 is in position, with the tip 15 of the second needle 13 (and the electrode lead 3 within the second needle 13) being positioned proximate to the nerve, and the tip 14 of the first needle 12 (and the housing portion 2 within the first needle 12) being positioned in the subcutaneous tissue, the second needle 13 can be partially retracted to a position between those shown in FIGS. 5A and 5B. In particular, the second needle 13 can be partially retracted to expose the electrodes (4, see FIG. 2) an the position of the electrodes can be tested. If needed, the second needle 13 can be re-extended to the position shown in FIG. 5A and repositioned.

Once the electrode lead 3 is appropriately positioned, the second needle 13 is retracted to the position shown in FIG. 5B to deploy the electrode lead 3.

The second needle 13 is retracted by unlocking the locking mechanism 17 and pulling on the actuation tab 16 relative to the handle 11 to slide the second needle 13 to the retracted position shown in FIG. 5B. The actuation tab 16 is pulled in a direction away from the patient. During retraction of the second needle 13 the handle 11 and first needle 12 remain stationary. As shown, once the second needle 13 is retracted the electrode lead 3 is deployed and exposed to the surrounding tissue (and nerve).

Next, as shown in FIG. 5C, the implant delivery device 10 is withdrawn from the patient and the housing portion 2 is deployed from the first needle 12. In this example the friction between the electrode lead 3 and the tissue (see muscle 8 in FIG. 2) is enough to hold the medical implant 1 in place as the implant delivery device 10 is withdrawn, thereby deploying the housing portion 2 out of the first needle 12 as the implant delivery device 10 is withdrawn from the patient.

In other examples the implant delivery device 10 may include a deployment member (e.g., a pusher in the first needle 12) configured to push the housing portion 2 out of the first needle 12. In some examples, the implant delivery device 10 may have a retaining member arranged to releasably attach the housing portion 2 to the first needle 12 and/or handle 11, and the retaining member can release the housing portion 2 after the second needle 13 is retracted and before the first needle 12 is removed from the patient.

Figure 7A:
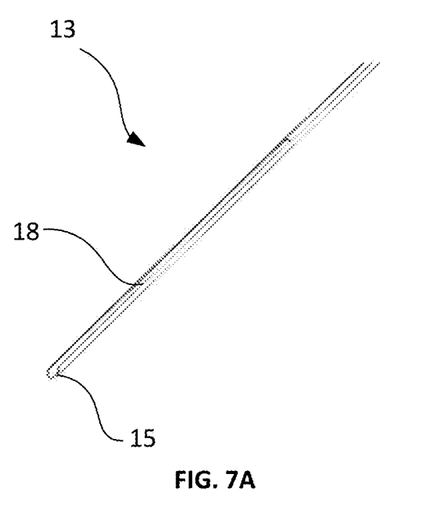
FIG. 7A shows the second needle.
Figure 7B:
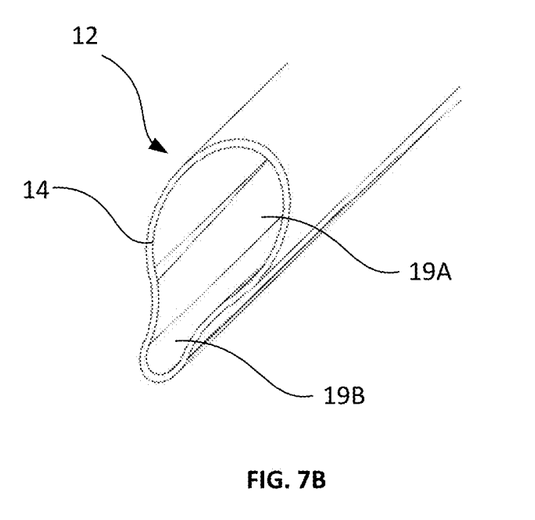
FIG. 7B shows the first needle.

FIGS. 6, 7A and 7B illustrate the first needle 12 and the second needle 13 of the delivery device 10 described above. As shown, the electrode lead 3 is received in the second needle 13, and the second needle 13 includes a slot 18 that allows the electrode lead 3 to connect to the housing portion 2 in the first needle 12. The slot 18 extends partially along the second needle 13 from the tip 15, and may extend the majority of the length of the second needle 13, or the entire length of the second needle 13. The second needle 13 may be in the form of a sheath. The first needle 12 receives the housing portion 2.

The first needle 12 includes a bevel tip 14. The second needle 13 includes a bevel tip 15. The bevel tips 14, 15 are sharp for piercing a patient's skin and penetrating the tissue during use.

As shown in FIG. 6, the second needle 13 extends through the lumen of the first needle 12. In particular, as shown in FIG. 7B the first needle 12 includes a primary portion 19A and a secondary portion 19B. The primary and secondary portions 19A, 19B are merged such that the first needle 12 has a single lumen. The primary and secondary portions 19A, 19B are shaped to define the two distinct portions 19A, 19B.

The primary portion 19A is shaped to receive the housing portion 2. In particular, the primary portion 19A is sized to receive the housing portion 2 and has a substantially circular cross-section that retains the housing portion 2 in axial alignment within the primary portion 19A.

The secondary portion 19B is shaped to receive the second needle 13. In particular, the secondary portion 19B is sized to receive the second needle 13 and has a substantially circular cross-section that retains the second needle 13 in axial alignment within the secondary portion 19B.

In examples, the secondary portion 19B and the primary portion 19A each have a substantially circular cross-section, and the cross-sections at least partially overlap. In such an example, the housing portion may be pushed over to one side of the primary portion 19A by the presence of the second needle 13 in the secondary portion 19B.

The slot 18 in the second needle 13 is directed towards the centre of the first needle 12, allowing the electrode lead 3 to connect with the housing portion 2 as shown in FIG. 6.

Accordingly, the first needle 12 is shaped to receive the housing portion 2 and the second needle 13, and to permit the second needle 13 to slide towards the retracted position. The position of the second needle 13 within the lumen of the first needle 1 beneficially means that there is only one puncture wound formed in the patient's skin, as the first needle 12 will enlarge the puncture wound formed by the second needle 13 during use.

In alternative examples the second needle 13 does not pass into, or through, the lumen of the first needle 12. Instead, the second needle 13 can extend through another part of the handle 11, for example adjacent to the first needle 12.

Figure 8:
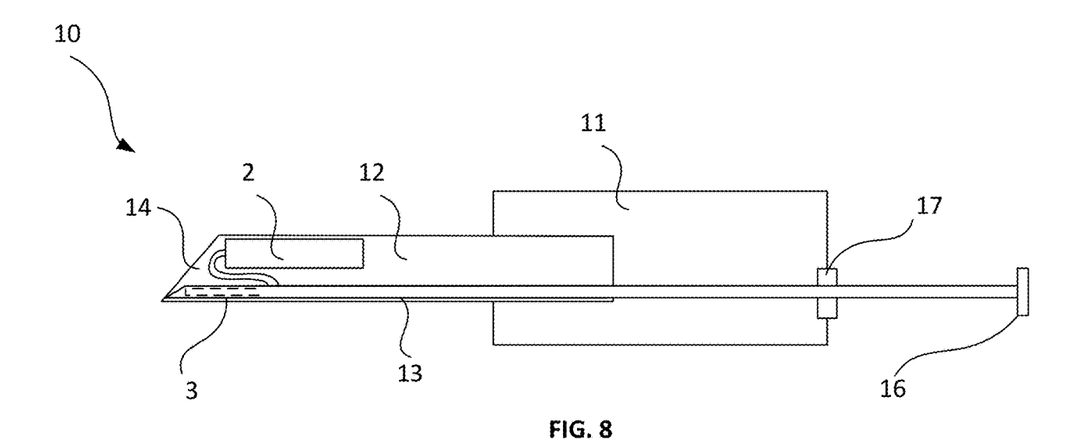
FIG. 8 shows an example delivery device in which the second needle is initially in a retracted position.

In the above-described examples the second needle 13 is initially in an extended position, and the first and second needles 12, 13 can be simultaneously positioned in the patient. FIG. 8 illustrates an alternative example in which the second needle 13 is initially in a retracted position. In this example, as shown, the actuation tab 4 extends from the handle 11. In the retracted position the second needle 13 may be within the first needle 12, as illustrated, or alongside the first needle 12 within the handle 11. The electrode lead 3 is partially within the second needle 13 and looped between the housing portion 2 and the second needle 13.

During implantation, the first needle 12 is inserted into the patient with the implant delivery device 10 in the configuration shown in FIG. 8, then the actuation tab 16 is pushed towards the handle 11 to extend the second needle 13 beyond the first needle 12 and carry the electrode lead 3 into position. In this position the locking mechanism 17 can be engaged such that the actuation tab 16 and second needle 13 are locked in position.

In some examples, the implant delivery device 10 may be removed from the patient with the second needle 13 in the extended position, and a deployment member (e.g., a pusher) may be provided to urge the medical implant 1 out of the first and second needles 12, 13. In other examples, after being extended the second needle 13 can then be retracted by pulling the actuation tab 16 away from the handle 11 in the manner described above with reference to FIGS. 5A to 5C, to release the electrode lead 3 and housing portion 2.

Figure 9:
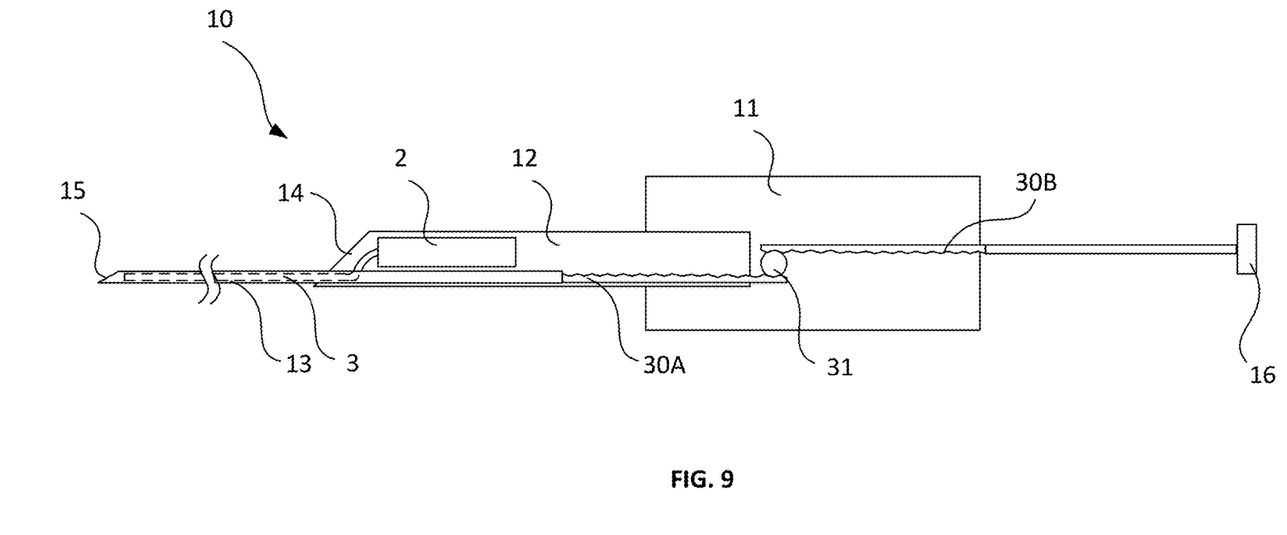
FIG. 9 shows an example delivery device in which the tab is moved towards the handle to retract the second needle.

FIG. 9 illustrates an alternative example delivery device 10. In this example the delivery device 10 comprises a handle 11, a first needle 12 holding the housing portion 2 and a second needle 13 holding the electrode lead 3, as previously described. In this example, the actuation tab 16 is arranged to be pushed towards the handle 11 (and the patient) in order to retract the second needle 13.

In particular, as illustrated, the implant delivery device 10 has a rack and pinion mechanism for translating movement of the actuation tab 16 towards the handle 11 into retraction of the second needle 13 (i.e., the second needle 13 moves in an opposite direction to the actuation tab 16).

As shown in FIG. 9, the rack and pinion mechanism comprises a first rack portion attached to, or formed as part of, the second needle 13. The rack and pinion mechanism also comprises a second rack portion 30B attached to, or formed as part of, the actuation tab 16. A pinion gear 31 is rotatably mounted within the handle 11 and is engaged with both the first and second rack portions 30A, 30B. The pinion gear 31 may be mounted within the first needle 12 or, as illustrated, behind the end of the first needle 12 within the handle 11. Accordingly, as the actuation tab 16 is pushed towards the patient the rack and pinion mechanism causes the second needle 13 to be retracted away from the patient to release the electrode lead 3.

Advantageously, pushing the actuation tab 16, rather than pulling the actuation tab 16, may permit one-handed operation of the implant delivery device 10.

Figure 10A:
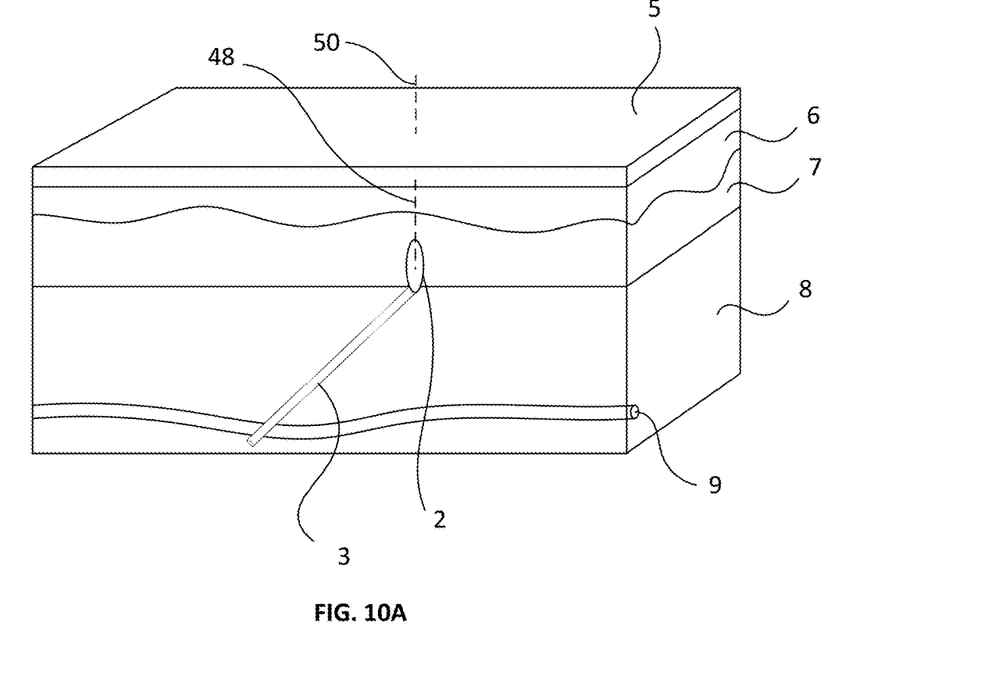
FIG. 10A shows a medical implant deployed in a first configuration relative to the skin surface.
Figure 10B:
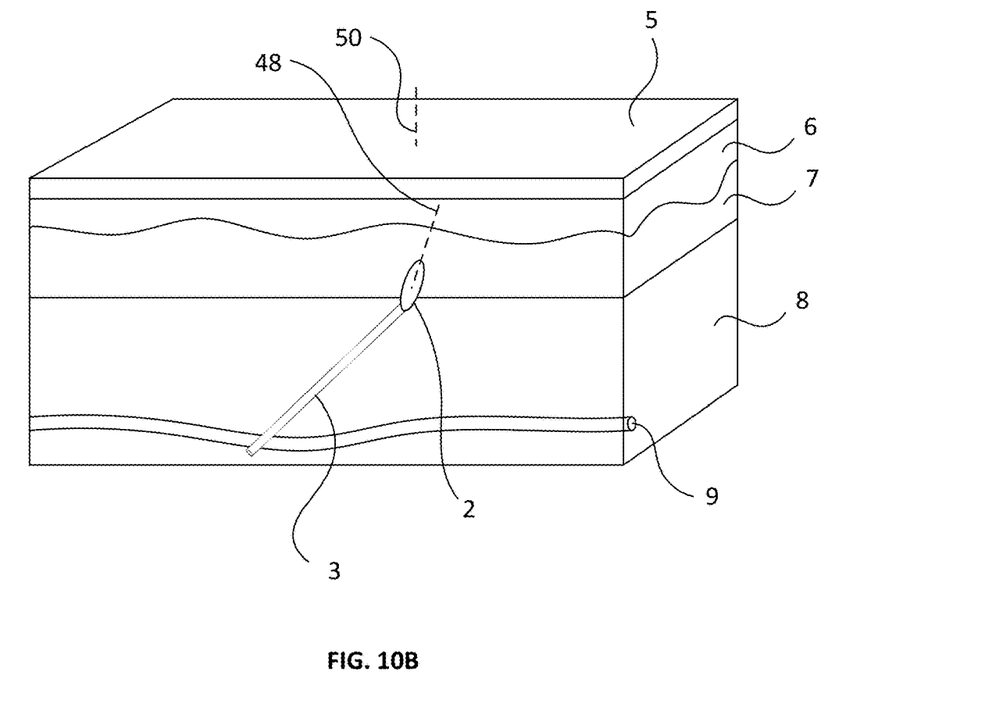
FIG. 10B shows a medical implant deployed in a second configuration relative to the skin surface.

FIGS. 10A and 10B show a medical implant 1 deployed in respective first and second configurations with the housing oriented such that the power-receiving direction is directed towards the skin surface (i.e. the epidermis 5) and the electrode 3 is extending towards the nerve 9 in a different direction to a longitudinal axis 48 of the housing portion 2.

For example, if an external device (32, see FIG. 2) with a wireless power transmitter is placed on the skin at the implantation site, it may transmit power most efficiently in a power transmitting direction 50 which may be in a perpendicular direction relative to the skin surface. As shown in FIGS. 10A and 10B, the electrode lead 3 is typically deployed at a greater depth than the housing portion 2, as the electrode lead 3 needs to be in close proximity to the nerve 9 to be stimulated, and the housing portion 2 needs to be closer to the surface for wireless power coupling and is thus typically implanted in subcutaneous tissue 7 of the patient.

The first configuration shows the housing portion 2 deployed with the longitudinal axis 48 substantially parallel to the power transmitting direction 50 of the wireless power transmitter of the external device (32, see FIG. 2), which will typically be the normal axis relative to the skin surface at the implantation site. The second configuration shows the housing portion 2 deployed with its longitudinal axis 48 at an acute angle relative to the power transmission direction 50 (e.g. the normal axis) at the implantation site.

The wireless power receiver of the medical implant 1 may have a power-receiving direction which is the direction of the wireless power receiver in which wireless power is most efficiently transferred. Assuming the power-receiving direction is perpendicular to the longitudinal axis 48 of the housing portion 2, the second configuration will exhibit smaller power losses compared to the first configuration, as the angle between the power-receiving direction and the power transmission direction 50 in the second configuration is less than that of the first configuration (where the power-receiving direction would be approximately 90 degrees relative to the power transmission direction). The smaller angle between power-receiving direction and power transmission direction 50 in the second configuration compared to the first configuration corresponds to more efficient power coupling between the wireless power receiver and the wireless power transmitter in the second configuration.

In this illustrated example, where the housing portion 2 is deployed such that the longitudinal axis 48 of the housing portion 2 is parallel with the skin surface, i.e. the power-receiving direction is parallel to the power transmission direction, this would provide particularly efficient power coupling.

In various examples, as illustrated in FIGS. 2, 10A and 10B, the electrode lead 3 is implanted at an angle relative to the skin 5, which may be necessary in order to avoid anatomical features or just to reach the desired implantation site. However, such an angle of the electrode lead 3 may not correspond to an efficient orientation of the housing portion 2 (and wireless power receiver 35, see FIG. 1) relative to the external device (32, see FIG. 2) and wireless power transmitter. Accordingly, as described variously below, the operator may implant the electrode lead 3 and housing portion 2 at different angles, and such that the wireless power receiver (35, see FIG. 1) is directed towards the skin 5 and thus also the external device (32, see FIG. 2).

Using the delivery devices illustrated above in relation to FIGS. 1 to 9, an operator is able to deploy the medical implant 1 with the housing portion 2 angled relative to the electrode lead 3 by retracting the second needle 13 (which initially contains the electrode 3), rotating the delivery device 10 such that the housing portion 2 is oriented in a desirable orientation relative to the skin surface, and deploying the housing portion 2 from the delivery device 10, for example using the pusher 40 as described above.

FIGS. 11 to 16 illustrate further exemplary delivery devices 10 able to deploy the medical implant 1 such that the housing portion 2 is oriented at an angle relative to the electrode lead 3. One or more of the structural components described above in relation to the delivery devices 10 illustrated in FIGS. 1 to 9 may be used in any of the delivery devices illustrated in FIGS. 11 to 16.

Figure 11:
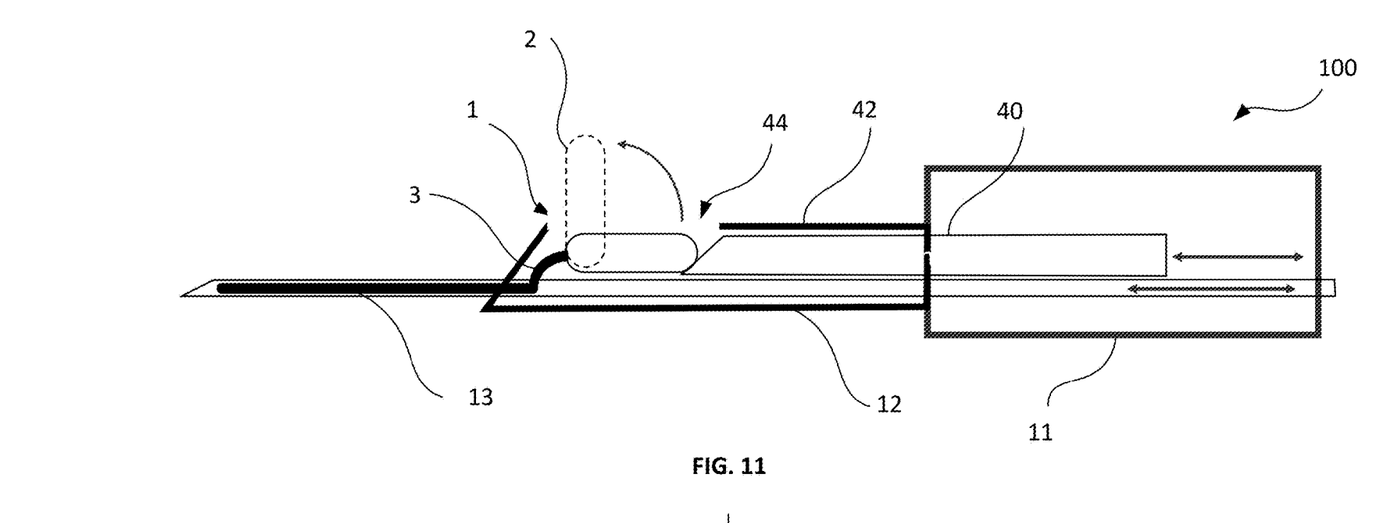
FIG. 11 shows a first example of an implant delivery device having a side opening through which a part of the medical implant can be ejected.

FIG. 11 illustrates an example of a delivery device 10 which can deploy the medical implant 1 in an alternative manner to that described above in relation to the delivery devices 10 illustrated in FIGS. 1 to 9.

The delivery device 10 of FIG. 11 includes a handle 11 and a delivery sheath. In this example the delivery sheath has a first part and a second part, in particular a first needle 12 and a second needle 13. The first 12 and second 13 needles in the delivery device 10 are configured in substantially the same way as described above and the specific features of the first 12 and second 13 needles will not be repeated here. The first needle 12 illustrated in FIG. 11 includes a side wall 42 having a side opening 44 formed therein. The side opening 44 may extend to the tip of the first needle 12, and in some examples may extend along the length of the first needle 12. The side opening 44 allows part or all of the medical implant 1 to be ejected through the side opening 44 in a non-parallel direction relative to an axial direction of the needle 12 as explained below. It would be apparent that a similar side opening 44 may be provided in the example implant delivery devices 10 described above in relation to FIGS. 1 to 9.

Figure 12:
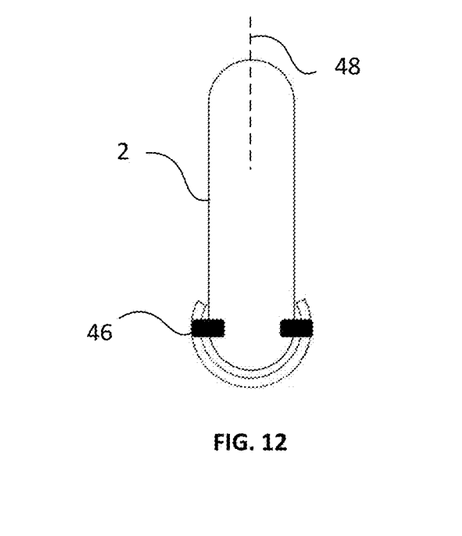
FIG. 12 shows a housing of the medical implant rotated to a second position.

In the example illustrated in FIG. 11, the delivery device 10 includes a deployment member (e.g. comprising a pusher 40) arranged to urge the housing portion 2 of the medical implant 1 out of the first needle 12 through the side opening 44 in the side wall 42. The deployment member can be deployed in the manner described above. When the pusher 40 initially contacts the housing portion 2, the housing portion 2 is arranged along the axial direction of the first needle 12. As the pusher 40 pushes against the housing portion 2, the housing portion 2 is rotated relative to the first needle 12, for example to a perpendicular angle relative to the first needle 12 as shown in FIGS. 11 and 12. The first needle 12 can include one or more guides 46 or pivot points to facilitate rotation of the housing portion 2.

Additionally or alternatively, the pusher 40 itself may be adapted to facilitate rotation of the housing portion 2, for example by including an end having a tapered cross-section. This allows the pusher 40 to also act as a wedge to rotate the housing portion 2 in a pre-determined direction (e.g. towards the side opening 44).

As the pusher 40 continues to push against the housing portion 2, eventually, the housing portion 2 is ejected from the first needle 12. The second needle 12 can then be retracted to deploy the electrode lead 3 as described above. It would be apparent the physician may rotate the delivery device 10 after the second needle 13 is retracted but before the housing portion 2 is ejected from the first needle 12 to orient the housing portion 2 in the desired orientation. Thus, the delivery device itself need not rotate the housing portion 2 to the final orientation before it is ejected from the first needle 12.

FIG. 12 illustrates the housing portion 2 in a rotated position relative to the axial direction of the first needle 12. In some examples, the housing portion 2 contains a wireless power receiver having an antenna receiver configured to receive power in a power-receiving direction. The power-receiving direction may be perpendicular to a longitudinal axis 48 of the housing portion 2. A separate antenna receiver is not essential, as in some cases, the housing portion 2 itself may be formed as a power-receiver with a power-receiving direction. In particular, a casing of the housing portion 2 may be conductive and arranged to act as a power-antenna receiver. In some examples, power may be wirelessly transmitted to the components within the housing portion 2 through a wireless power transmission window formed in the housing portion 2. When a wireless power transmission window is present, it is preferable to deploy the housing portion 2 such that the wireless power transmission window is directed towards the skin of the patient at the implantation site.

Being able to deploy the medical implant 1 with the housing portion 2 oriented in a different direction to the electrode lead 3 is desirable due to the power losses associated with wireless power coupling when the power-receiving direction is not aligned with the power transmission direction of an external device (32, see FIG. 2).

Figure 13:
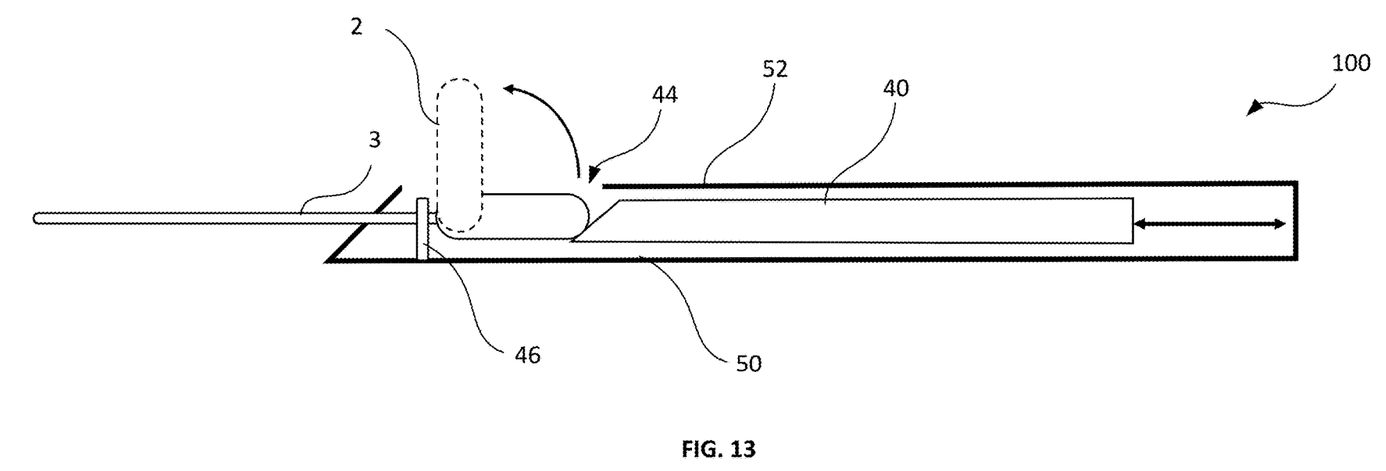
FIG. 13 shows a second example of a delivery device with a side opening.

FIG. 13 shows a second example of the delivery device 10 with a side opening 44. The delivery device 10 illustrated in FIG. 13 differs from the delivery device 10 illustrated in FIG. 11 as the delivery sheath comprises a cannula 50 instead of first and second needles 12, 13. The medical implant 2, 3 is received in the cannula 50, which is percutaneously positioned during implantation. Once the cannula 50 has been percutaneously positioned the pusher 40 pushes the medical implant 2, 3 out of the cannula 50. The cannula 50 can be simultaneously withdrawn while the pusher 40 pushes the medical implant 2, 3 out of the cannula 50.

The cannula 50 includes a side wall 52 with a side opening 44 formed therein to allow the housing portion 2 to be ejected in the manner described above with reference to FIGS. 11 and 12. The side opening 44 preferably extends to the tip of the cannula 50 and allows the electrode lead 3 to pass therethrough. In some examples, the side opening 44 may extend along the length of the cannula 50. It would be apparent the side opening 44 could have different widths along the length of the cannula 50. For example, the width of the side opening 44 may be larger at a proximal section of the cannula 50 where the housing portion 2 needs to be accommodated, but at a distal section, where the electrode lead 3 needs to be accommodated, the opening may be smaller. Thus, as the cannula 50 is retracted, the electrode lead 3 can be deployed, and as the pusher 40 is pushed, the housing portion 2 can be ejected through the side opening 44 with the power-receiving direction oriented towards to the skin surface. The illustrated cannula 50 includes one or more guides 46 or pivot points which facilitate rotation of the housing portion 2. As with the example of FIG. 11, the pusher 40 is also shaped to facilitate rotation of the housing portion 2 and the description above in relation to the pusher 40 apply equally to FIG. 13.

Figure 14:
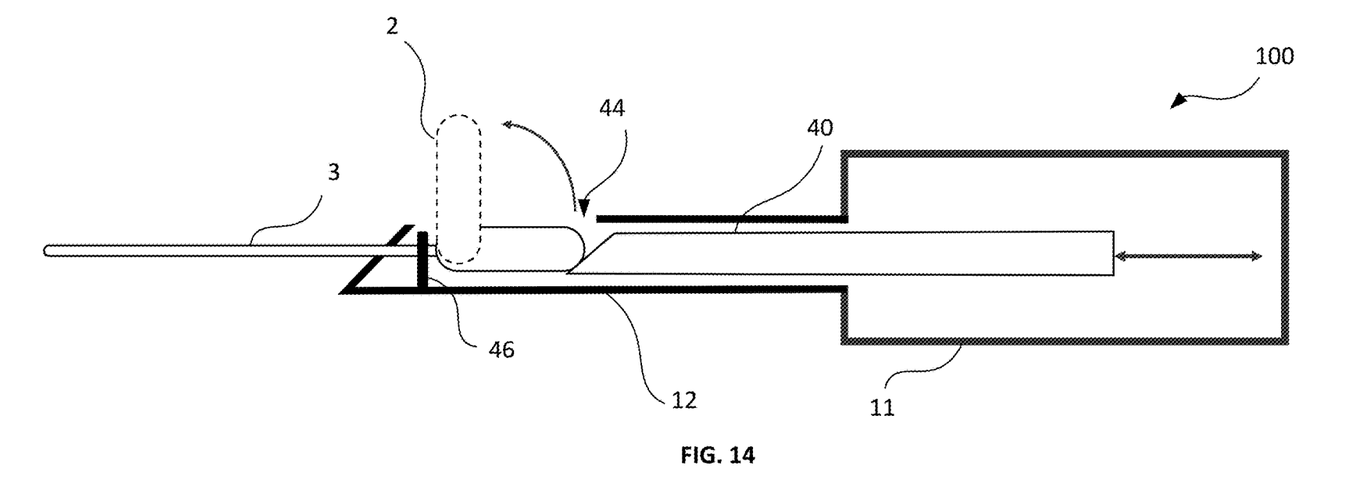
FIG. 14 shows a third example of a delivery device with a side opening.

FIG. 14 shows a third example of a delivery device 10 with a side opening 44. The delivery device 10 illustrated in FIG. 14 differs from the delivery device 10 illustrated in FIG. 11 as the delivery sheath comprises a single needle 12. The needle 12 has substantially the same features as the cannula 50 of the delivery device 10 illustrated in FIG. 12, and the description provided above in relation to those features apply equally to the delivery device 10 illustrated in FIG. 14. The needle 12 of the example of FIG. 14 may have a bevel tip allowing the needle 12 to puncture the patient's skin and tissue without the need for an incision.

Figure 15:
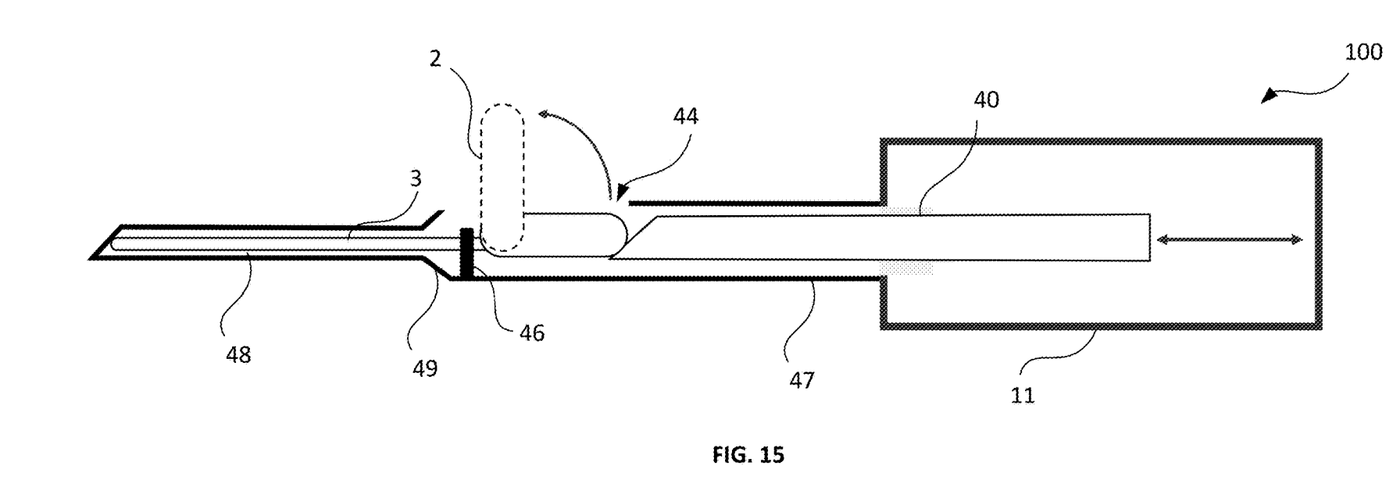
FIG. 15 shows a fourth example of a delivery device with a side opening.

FIG. 15 shows a fourth example of a delivery device 10 with a side opening 44. The delivery device 10 illustrated in FIG. 15 has a delivery sheath formed of a first portion 47 and a second portion 48. The first portion 47 is sized to receive the housing portion 2, and the second portion 48 extends from the first portion 47 and is fixed thereto. The first portion 47 comprises a side opening 44. The side opening 44 may extend to the join of the first portion 47 and the second portion 48, and in some examples may extend along the length of the first portion 47. The side opening 44 may extend into the second section 48 and optionally to the tip of the second section 48. The second portion 48 has a smaller diameter than the first portion 47 and holds the electrode lead 3. A tapered section 49 joins the first and second portions 47, 48. The tapered section 49 may be shaped to guide the housing portion 2 out of the side opening 44 in the first portion 47. The tapered section 49 in the delivery sheath advantageously rotates the housing 2 as it slides out of the side opening 44 as it is pressed by the pusher 40. A guide 46 as described with reference to FIGS. 12 and 13 may additionally be provided to guide and rotate the housing portion 2 as previously described. In some cases, the guide 46 may be omitted.

Figure 16:
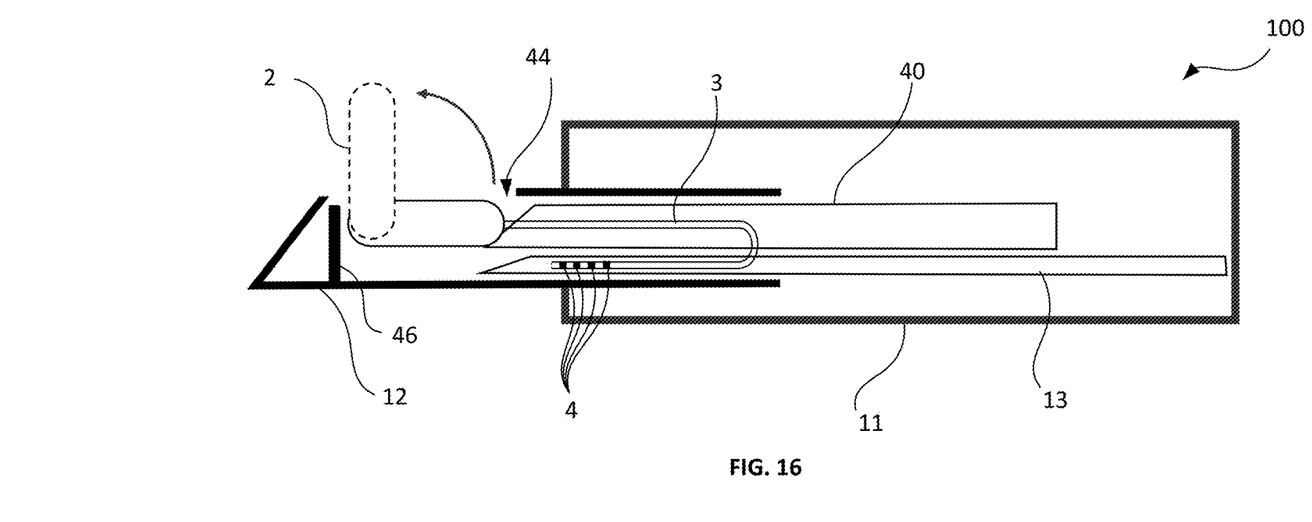
FIG. 16 shows a fifth example of a delivery device with a side opening.

FIG. 16 shows a fifth example of a delivery device 10 with a side opening 44. In this example the delivery device 10 has a delivery sheath with a first needle 12 and a second needle 13 that is movable, in particular extendible and retractable, relative to the first needle 12 in the same manner as described with reference to FIGS. 4 to 9. In this example, the second needle 13 is initially retracted relative to the first needle 12 so that the first needle punctures the skin to deploy the housing portion 2 before the electrode 3 is deployed. The housing 2 is deployed via the pusher 40 as described above. Once the housing portion 2 is deployed in the desired orientation, the second needle 13 can be extended to position the electrode lead 3 in close proximity to the nerve 9. An opening formed in the second needle 13 as described above allows the electrode lead 3 to pass through the second needle 13 as the second needle 13 is extended deeper into the tissue towards the nerve 9. The side opening 44 in the side wall of the first needle 12 may also extend to the distal tip of the first needle 12 although this is not essential. The side opening 44 may extend along the length of the first needle 12. Once the electrode lead 3 is in position, the second needle 13 can be withdrawn to deploy the electrode lead 3.

At various places in the present specification, values are disclosed in groups or in ranges. It is specifically intended that the description include each and every individual sub-combination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Similarly, for example, a real number in the range of 0.00 to 40.00 is specifically intended to individually disclose all real numbers between 0.00 and 40.00.

Throughout the description and claims of this specification, the words "comprise" and "contain" and variations of them mean "including but not limited to", and they are not intended to (and do not) exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A method of percutaneously implanting a medical implant in tissue of a patient using a delivery device, wherein the delivery device comprises a delivery sheath, the medical implant comprising an elongate electrode lead and a housing portion holding a wireless power receiver comprising an antenna receiver for receiving wireless power by wireless power coupling wherein the delivery sheath comprises a first needle and a second needle and intially during use the housing portion is received in the first needle and the electrode leade is received in the second needle, the method comprising:

deploying the electrode lead by retracting the second needle;

rotating the delivery device such that the housing portion is oriented in a desirable orientation relative to the skin surface; and deploying the housing portion from the delivery device to percutaneously implant the medical implant such that a power receiving direction of the antenna is oriented towards the skin surface of the patient at the implantation site.

2. The method of claim 1, comprising percutaneously implanting the medical implant such that the wireless power receiver is oriented within about 20 degrees of a normal line from the skin surface of the patient at the implantation site.

3. The method of claim 1, comprising percutaneously implanting the medical implant such that the wireless power receiver is oriented substantially parallel to a normal line from the skin surface of the patient at the implantation site.

4. The method of claim 1, comprising percutaneously implanting the medical implant such that the wireless power receiver is oriented within about 5 degrees of the normal line from the skin surface of the patient at the implantation site.

5. The method of claim 1, wherein the medical implant comprises an elongate housing portion holding the wireless power receiver, and wherein the wireless power receiver is oriented substantially perpendicularly to the elongate housing portion.

6. The method of claim 5, comprising percutaneously implanting the medical implant such that the housing portion is substantially parallel to the skin surface of the patient at the implantation site.

7. The method of claim 5, wherein the housing portion comprises a wall having a wireless power transmission window for transmission of wireless power through the wall of the housing portion, and wherein the method comprises percutaneously implanting the medical implant such that the wireless power transmission window is directed towards the skin of the patient at the implantation site.

8. The method of claim 5, comprising simultaneously percutaneously implanting the housing portion and the electrode lead.

9. The method of claim 5, comprising percutaneously implanting the electrode lead at a greater depth than the housing portion.

10. The method of claim 5, comprising percutaneously implanting the electrode lead proximal to a nerve of the patient, and percutaneously implanting the housing portion in subcutaneous tissue of the patient.

11. The method of claim 1, wherein the medical implant comprises an elongate housing portion holding the wireless power receiver, and wherein the method comprises percutaneously implanting the electrode lead at a non-parallel angle relative to the elongate housing portion.

12. The method of claim 11, comprising percutaneously implanting the elongate housing portion such that an axial direction of the electrode lead is approximately perpendicular to the elongate housing portion.

13. The method of claim 11, comprising percutaneously implanting the electrode lead while the elongate housing portion is substantially parallel to the electrode lead, and, once the electrode lead is implanted, positioning the elongate implant housing such that the wireless power receiver is oriented towards the skin of the patient at the implantation site.

14. The method of claim 1, further comprising percutaneously positioning the delivery sheath to percutaneously implant the medical implant.

15. The method of claim 14, wherein the second needle of the delivery sheath is parallel with and extends beyond the first needle of the delivery sheath.

16. The method of claim 15, wherein the second needle of the delivery sheath is retractable relative to the first needle of the delivery sheath, and wherein the method comprises percutaneously positioning the first needle of the delivery sheath at a first depth, percutaneously positioning the second needle of the delivery sheath at a second depth, retracting the second needle of the delivery sheath to implant the electrode lead, and ejecting the housing portion from the first needle of the delivery sheath.

17. The method of claim 16, wherein the first part of the delivery sheath has an axial direction, and wherein the housing portion is ejected from the first part of the delivery sheath in a direction non-parallel to axial direction of the first part of the delivery sheath.

18. The method of claim 17, wherein the housing portion is ejected from the first part of the delivery sheath through a side opening in the first part of the delivery sheath.

19. The method of claim 16, wherein the housing portion is rotated as it is ejected from the first part of the delivery sheath.

20. The method of claim 16, wherein the delivery device comprises a pusher operable to eject the housing portion from the first part of the delivery sheath, and wherein the method comprises operating the pusher to eject the housing portion from the first part of the delivery sheath.

21. The method of claim 1, wherein the medical implant comprises a neurostimulator implant or a diagnostic implant.

22. The method of claim 1, wherein the medical implant further comprises a wireless power transmitter, and wherein the medical implant is operable as a wireless power relay for providing wireless power to a further medical implant.

23. The method of claim 1, comprising percutaneously implanting the medical implant such that the wireless power receiver is oriented within about 10 degrees of the normal line from the skin surface of the patient at the implantation site.

* * * * *